(12) United States Patent
Wolf

(10) Patent No.: US 6,886,423 B2
(45) Date of Patent: May 3, 2005

(54) SCALABLE, AUTOMATED METROLOGY SYSTEM AND METHOD OF MAKING THE SYSTEM

(75) Inventor: Robert Gregory Wolf, Hackettstown, NJ (US)

(73) Assignee: Rudolph Technologies, Inc., Flanders, NJ (US)

( * ) Notice: Subject to any disclaimer, the term of this patent is extended or adjusted under 35 U.S.C. 154(b) by 0 days.

(21) Appl. No.: 10/397,326

(22) Filed: Mar. 27, 2003

(65) Prior Publication Data

US 2004/0040380 A1 Mar. 4, 2004

Related U.S. Application Data

(60) Provisional application No. 60/367,511, filed on Mar. 27, 2002.

(51) Int. Cl.$^7$ .......................... G01D 21/00; G01B 11/24
(52) U.S. Cl. .......................... 73/866.5; 702/83; 356/601
(58) Field of Search .......................... 702/83, 155, 167; 356/601, 632; 73/866.5, 104, 105, 431

(56) References Cited

U.S. PATENT DOCUMENTS

| | | | |
|---|---|---|---|
| 4,710,030 A | | 12/1987 | Tauc et al. |
| 6,283,692 B1 | * | 9/2001 | Perlov et al. .......... 414/222.01 |
| 6,346,426 B1 | * | 2/2002 | Toprac et al. .................. 438/8 |
| 6,633,831 B2 | * | 10/2003 | Nikoonahad et al. ....... 702/155 |
| 2002/0152808 A1 | * | 10/2002 | Tegeder et al. .......... 73/170.16 |
| 2002/0176074 A1 | * | 11/2002 | Hasan ...................... 356/237.5 |
| 2003/0112445 A1 | * | 6/2003 | Evans et al. ................ 356/498 |
| 2004/0007325 A1 | * | 1/2004 | Pan et al. ................ 156/345.1 |

\* cited by examiner

Primary Examiner—Helen C. Kwok
(74) Attorney, Agent, or Firm—Antonelli, Terry, Stout & Kraus, LLP

(57) ABSTRACT

An automated metrology system for photoacoustic measurement of single or multi-layer films, and a method of making the system, are disclosed. Dramatic improvements in the cost of ownership of the system is attained by making the system scalable from a system having a single metrology sub-system for making measurements, to a system having two, vertically stacked metrology sub-systems for making independent measurements. A front end of the system for storing multiple cassettes comprises a robot having vertical travel capable of transferring cassettes to and from each of the first and second metrology sub-systems in the case the system is expanded. The two metrology sub-systems are preferably identical and share much of the optics, a computer as well as the front end of the system. Throughput of the dual system is 1.75–2 times greater than that of a single tool metrology system while the cost is substantially less than two complete single tool metrology systems.

17 Claims, 2 Drawing Sheets

SCALABLE, AUTOMATED METROLOGY SYSTEM AND METHOD OF MAKING THE SYSTEM

RELATED APPLICATION

This application claims priority of provisional application Ser. No. 60/367,511 filed Mar. 27, 2002, the disclosure of which is incorporated by reference.

TECHNICAL FIELD

The present invention relates to thin film metrology and more particularly, to an improved automated metrology system which uses photoacoustic measurement for the measurement of thicknesses and adhesion properties of thin films. The invention dramatically lowers the cost of ownership of such a system.

BACKGROUND

Photoacoustic systems for measuring the thicknesses and adhesion properties of metal and opaque films in a film stack on a substrate are well known. An optical generator and detector of stress pulses useful in such photoacoustic systems in disclosed in U.S. Pat. No. 4,710,030 to Tauc et al. A schematic diagram of one arrangement of an optical stress-pulse generation and detection system 34 is shown in FIG. 1. The system 34 includes radiation source 36 for providing pulsed pump beam PM and radiation source 38 for providing a continuous probe beam PB. The wavelength of the pump beam PM is selected so that it is strongly absorbed in the particular film to be studied or in a medium associated with the film.

Pump beam PM and probe beam PB are directed to film 40 through lens 42. Mirrors 44, 46 and 48, 50 direct pump beam PM and probe beam PB, respectively, to lens 42. The portion of pump beam PM that is not absorbed by film 40 is reflected as ray 52 and prevented from reaching photodector 54 by beam-blocker 56. When the induced stress pulse returns to the surface of film 40 it causes a slight variation in reflectivity which changes the intensity of reflected ray 58 of continuous probe beam PB. The photodector 54 has a sufficiently short response time to respond to the fast changes in reflectivity. The output of detector 54 is displayed in sampling oscilloscope 60 as a function of time. Signal averager 62, interfaced with oscilloscope 60, integrates the responses over many pump beam pulses and improves the signal-to-noise ratio. Examples of other optical stress pulse generation and detection systems for photoacoustic systems for measuring thin film are disclosed in the patent to Tauc et al.

An example of an implementation of the photoacoustic measurement technology of the Tauc et al. patent in an automated metrology system 51 useful for measuring thicknesses of metal films on wafers by semiconductor manufacturers is shown in the block diagram of FIG. 2. The metrology system 51 includes measurement stage 61, robotics and wafer handling system 65, measurement system 75, cassette station 70, computer controller 55, and communication lines 80. Computer controller (controller) 55 is electrically connected to measurement system 75, measurement stage 61, robotics and wafer handling system 65, and cassette station 70 via communication lines 80. Controller 55 further includes software embodied in a computer-readable medium capable of carrying out the steps of the measurement method.

In a typical operation, controller 55 sends an instruction to the robotics and wafer handling system 65 to extract a wafer from cassette station 70, and to position the wafer on the measurement stage 61. The controller 55 then issues commands to the measurement stage 61 to position the wafer relative to the measurement system so that measurements can be made at a predetermined location. The measurement stage includes a test surface upon which the wafer is placed for measurements and translation stages to provide wafer manipulation in three degrees of freedom. The controller 55 then issues commands to the measurement system 75 to make a measurement and display the results of the measurement. Once the measurement is complete, controller 55 issues instructions to the robotics and wafers handling system 65 to return the wafer to the cassette station 70.

The assignee of the present application, Rudolph Technologies, Inc., manufacturers automated metrology systems which operate in accordance with the system 51 shown in block diagram in FIG. 2. These systems are marketed under assignee's registered trademark MetaPULSE, and are particularly useful by semiconductor manufacturers as film thickness metrology tools for 200 mm and 300 mm wafers.

The automation platform of the known automated metrology systems is shown in FIG. 3. As depicted in FIG. 3, the metrology system 51 comprises a single measurement tool or metrology 90 in which the measurement stage 61 and measurement system 75, FIG. 3, are located. The robotics and wafer handling system 65 and cassette station 70 are located in a front end 91 of the system. Electronics unit 92 contains the computer controller 55. A front opening unified pod (FOUP) 93 is used with the system to protect and transport wafers having films to be measured.

There is a continuous, strong desire by semiconductors manufacturers to find ways to increase their rate of production and, at the same time, to lower their production costs. There is a need for an improved automated metrology system which would do both.

DETAILED DESCRIPTION OF DISCLOSED EMBODIMENT

Figure 1:
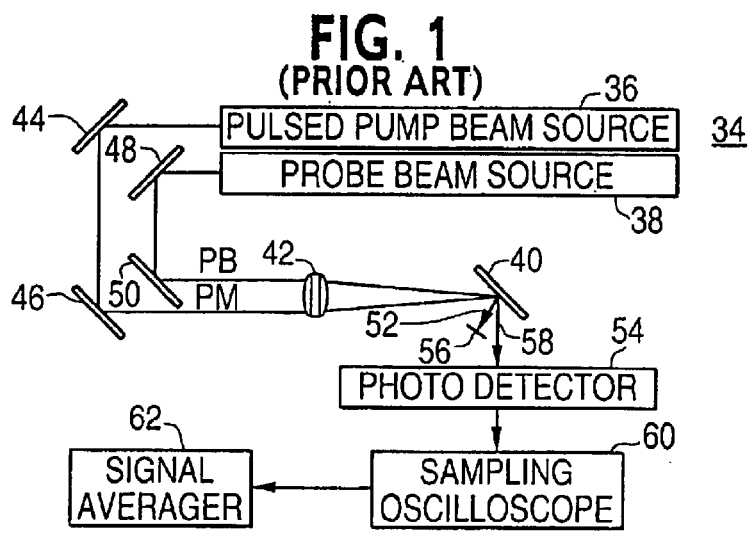
FIG. 1 is a schematic diagram of a known optical stress pulse generation and detection system according to the patent to Tauc et al., U.S. Pat. No. 4,710,030.

The present invention is a method and an automated metrology system that dramatically improve the cost of ownership of an automated metrology system for photoacoustic measurement. To this end, the method of the invention comprises making an automated metrology system, 100 in FIG. 4, which is scalable from a system having a single metrology sub-system 101 for making measurements to a system having two, vertically stacked metrology sub-systems, 101 and 102, for making measurements, and providing the system with a front end, 103 for storing multiple cassettes and transferring the wafers stored in the cassettes to and from either the single metrology sub-system 101 or both of the vertically stacked metrology sub-systems, 101 and 102, of the system.

The system 100 is expandable without changing the size or form-factor of the system. The front end 103 includes a robot 104 having vertical travel capable of transferring wafers stored in the cassettes from cassette station 70 to and from each of the first and second metrology sub-systems 101 and 102 in the case the system is expanded to include the second metrology sub-system.

The system 100 further includes in combination a front opening unified pod (FOUP) 105 to protect and transport wafers having films to be measured. The FOUP 105 has a capacity to service both the first and second metrology sub-systems 101 and 102 with only a slight delay for one of the two sub-systems in the case the system is expanded to include the second metrology sub-system. Each sub-system is capable of completely independent measurements. When the system 100 is expanded to include the second sub-system 102, the system 100 has a throughput or measurement speed of 1.75–2 times greater than with the use of the system when unexpanded, e.g. with only a single metrology sub-system 101.

Figure 2:
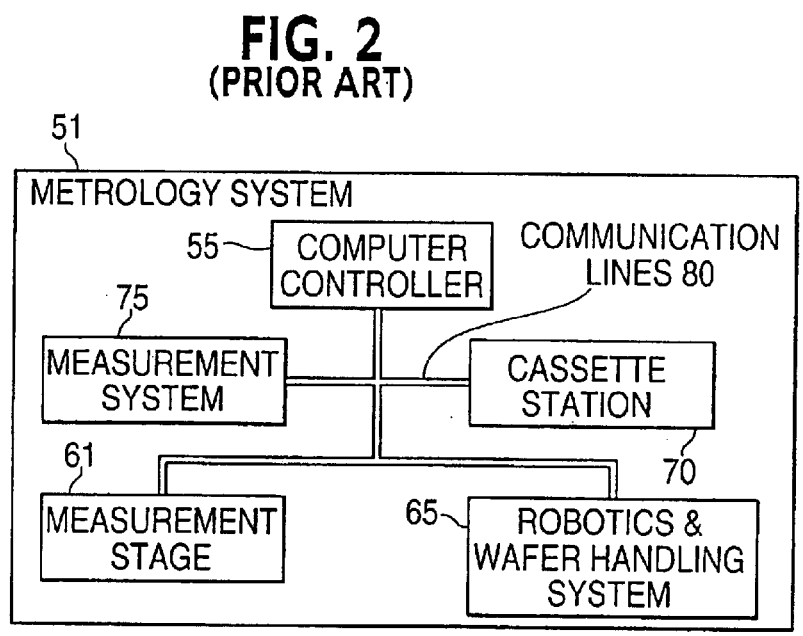
FIG. 2 is a block diagram of a known automated metrology system for photoacoustic measurement in accordance with principles of the Tauc et al. patent.
Figure 3:
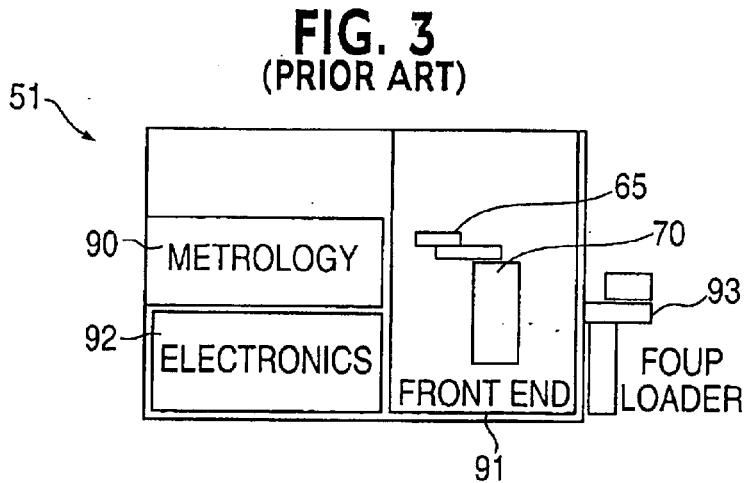
FIG. 3 is a schematic diagram of the automation platform of the known automated metrology of FIG. 2.

An electronics unit 106 of the system 100 contains components capable of being shared by the first and second metrology sub-systems in the case the system is expanded to include the second metrology sub-system. The electronics unit 106 is also capable of accommodating additional components associated with the second metrology sub-system in the case the system is expanded. More specifically, in the example embodiment the two metrology sub-systems 101 and 102 are identical measuring heads, each with a measurement stage and measurement system as described with reference to FIG. 2. Each of the sub-systems shares much of the optics, the computer in the electronics unit 106 and the front end 103 as noted above. Additional boards can also be provided in the computer as well as a second processor when the second metrology sub-system 102 is added to the system.

Figure 4:
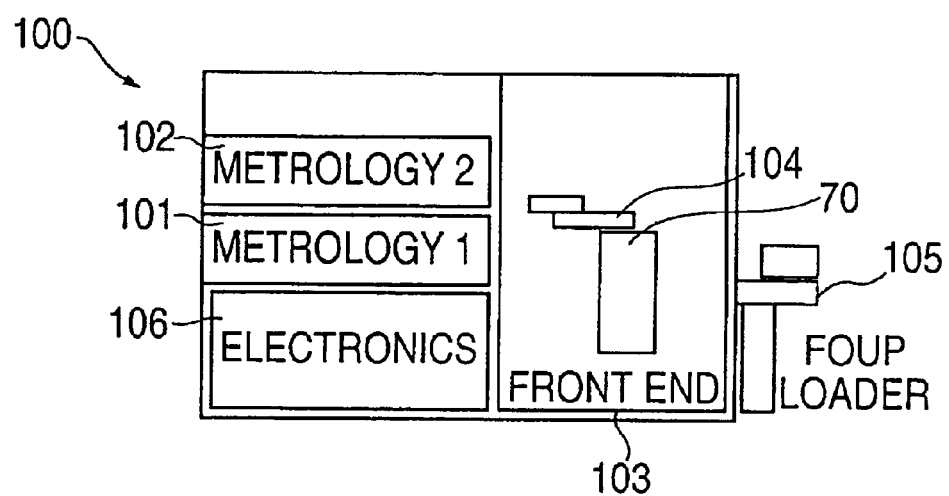
FIG. 4 is a schematic diagram of the automation platform of the improved automated metrology system of the present invention.

In the expanded state of the system 100, as shown in FIG. 4, the system is a dual, automated metrology system which has the same size and form-factor as a single, metrology, tool but measures 1.75–2 times the speed by incorporating the two completely independent measuring sub-systems. Because of the cost savings of a single front end and selected internal components as noted, the system costs less than two complete conventional automated metrology systems for photoacoustic measurement.

The two metrology sub-systems 101 and 102 in the dual system 100 are preferably matched and can be used together on one cassette to double the system throughput, or on separate cassettes to process two different lots simultaneously. Cost of ownership is dramatically improved because the dual system 100 requires the same facilities hookup as a single tool and has the same consumable rate as one tool. The system is also advantageous in that it can be purchased with only one metrology sub-system for future expansion or with both metrology sub-systems for full capacity. When purchased with only one metrology sub-system, future fab expansion or process ramp can be accomplished with no extra footprint or facilities requirement.

While I have shown and described only a single example embodiment in accordance with the invention, it should be understood that the invention is not limited thereto but is susceptible to various changes and modifications as will be apparent to the skilled artisan.

I claim:

1. A scalable, automated metrology system for photoacoustic measurement, the system comprising:
    a first photoacoustic metrology sub-system for making measurements;
    a front end for storing multiple cassettes and transferring wafers stored in the cassettes to and from the first photoacoustic metrology sub-system;
    wherein the system is expandable to include a second photoacoustic metrology sub-system for making measurements, with the first and second photoacoustic metrology sub-systems in vertically stacked relation to one another and sharing system optics, a computer and the front end to provide a system throughput which is 1.75 to 2 times greater when expanded compared with that when unexpanded.

2. The automated metrology system according to claim 1, wherein the system is expandable without changing the size or form-factor of the system.

3. The automated metrology system according to claim 1, wherein the front end includes a robot having vertical travel capable of transferring wafers stored in the cassettes to and from each of the first and second metrology sub-systems in the case the system is expanded to include the second metrology sub-system.

4. The automated metrology system according to claim 1, further comprising in combination a front opening unified pod (FOUP) to protect and transport wafers having films to be measured, the FOUP having the capacity to service both the first and second metrology sub-systems with only a slight delay for one of the first and second sub-systems in the case the system is expanded to include the second metrology sub-system.

5. The automated metrology system according to claim 1, wherein the first and second metrology sub-systems, in the case the system is expanded, are completely independent measuring sub-systems.

6. The automated metrology system according to claim 1, further comprising an electronics unit for the system, the electronics unit containing components capable of being shared by the first and second metrology sub-systems in the case the system is expanded to include the second metrology sub-system.

7. The automated metrology system according to claim 6, wherein the electronics unit is capable of accommodating additional components associated with the second metrology sub-system in the case the system is expanded.

8. A dual, automated metrology system for photoacoustic measurement, the system comprising:
    a first photoacoustic measuring head with a measurement stage and a measurement system for making measurements;
    a second photoacoustic measuring head with a measurement stage and a measurement system for making measurements, the second measuring head being arranged in vertically stacked relation to the first measuring head; and
    a front end for storing multiple cassettes and transferring wafers stored in the cassettes to and from the first and second measuring heads for making measurements;
    wherein the first and second measuring heads share system optics, a computer and the front end to provide a system throughput which is 1.75 to 2 times greater compared with that of a system with a single photoacoustic measuring head.

9. The automated metrology system according to claim 8, further comprising in combination a front opening unified pod (FOUP) to protect and transport wafers having films to be measured, the FOUP having the capacity to service both the first and second photoacoustic measuring heads with only a slight delay for one of the first and second measuring heads.

10. The automated metrology system according to claim 8, wherein the system has the same size and form-factor as a single metrology tool for making measurements.

11. The automated metrology system according to claim 8, wherein the front end includes a robot having vertical travel capable of transferring wafers stored in the cassettes to and from each of the first and second measuring heads.

12. The automated metrology system according to claim 8, wherein the first and second measuring heads are completely independent measuring heads.

13. The automated metrology system according to claim 8, further comprising an electronics unit for the system, the electronics unit containing components which are shared by the first and second measuring heads.

14. The automated metrology system according to claim 8, wherein the first and second measuring heads are matched and can be used together for making measurements on wafers in one cassette to double a system throughput, or on wafers in separate cassettes to process two different lots simultaneously.

15. The automated metrology system according to claim 8, wherein the system has the same facilities hookup requirements as a system having a single metrology tool.

16. The automated metrology system according to claim 8, wherein the first and second metrology heads are identical.

17. A method of dramatically improving the cost of ownership of an automated metrology system for photoacoustic measurement, the method comprising:

making an automated photoacoustic metrology system which is scalable from a system having a single photoacoustic measuring head for making measurements to a system having two, vertically stacked photoacoustic measuring heads for making measurements wherein the two measuring heads share system optics and a computer, and providing the system with a front end for storing multiple cassettes and transferring wafers stored in the cassettes to and from either a single photoacoustic measuring head or two vertically stacked photoacoustic measuring heads, of the system, wherein a system throughput is 1.75 to 2 times greater compared with that of a system with a single photoacoustic measuring head.

* * * * *